United States Patent
Rosen et al.

(10) Patent No.: US 6,329,148 B1
(45) Date of Patent: Dec. 11, 2001

(54) COMBINED THERAPY OF DITERPENOID TRIEPOXIDES AND DEATH DOMAIN RECEPTOR LIGANDS FOR SYNERGISTIC KILLING OF TUMOR CELLS

(75) Inventors: Glenn D. Rosen; Peter Kao, both of Stanford, CA (US)

(73) Assignee: The Board of Trustees of the Leland Stanford University, Palo Alto, CA (US)

(*) Notice: Subject to any disclaimer, the term of this patent is extended or adjusted under 35 U.S.C. 154(b) by 0 days.

(21) Appl. No.: 09/505,250

(22) Filed: Feb. 15, 2000

Related U.S. Application Data

(60) Provisional application No. 60/120,313, filed on Feb. 16, 1999, and provisional application No. 60/149,989, filed on Aug. 20, 1999.

(51) Int. Cl.[7] ............... C12Q 1/68; A01N 65/00; A61K 48/00

(52) U.S. Cl. ............... 435/6; 424/78; 424/195.1; 514/44; 514/469

(58) Field of Search ............... 435/6; 424/195.1, 424/78; 514/469, 44

(56) References Cited

U.S. PATENT DOCUMENTS

| | | | |
|---|---|---|---|
| 5,759,550 | * | 6/1998 | Wiedmann et al. ............... 424/195.1 |
| 5,994,298 | | 11/1999 | Tsai et al. . |

FOREIGN PATENT DOCUMENTS

| | | | |
|---|---|---|---|
| wo9426265 | * | 11/1994 | (WO) . |
| wo9731921 | * | 2/1997 | (WO) . |
| 97/31921 | | 9/1997 | (WO) . |
| 98/52951 | | 11/1998 | (WO) . |

OTHER PUBLICATIONS

Shamon, Lisa A., et al., "Evaluation of the Mutagenic, Cytotoxic, and Antitumor Potential of Triptolide, a highly Oxygenated Diterpene Isolated from Tripterygium Wilfordii," Cancer Letters (1997) vol. 112:113–117.*

Wiley, Steven R., et al., "Identification and Characterization of a New Member for the TNF Family that Induces Apoptosis," Immunity (1995) vol. 3:673–682.*

Walczak, Hening et al., "Tumoricidal Activity of Tumor Necrosis Factor–Related Apoptosis–Inducing Ligand In Vivo," Immunity (Feb. 1999) vol. 5(2): 157–163.*

Lee, K.Y et al., "PG490(Triptolide) Cooperates with Tumor Necrosis Factor to Induce Apoptosis in Tumor Cells," Biological Chemistry, vol.274, No. 19, 1999 pp. 13451–13455.*

Lee et al, (May 7, 1999), "PG490 (Triptolide) Cooperates with Tumor Necrosis Factor–α to Induce Apoptosis in Tumor Cells," *Journal of Biological Chemistry*, vol. 274(19):13451–13455.

Keane et al. (Feb. 1, 1999), "Chemotherapy Augments TRAIL–Induced Apoptosis in Breast Cell Lines," *Cancer Research*, vol. 59:734–741.

(List continued on next page.)

Primary Examiner—W. Gary Jones
Assistant Examiner—Fariba Ghashghaee
(74) Attorney, Agent, or Firm—Pamela J. Sherwood.; Bozicevic, Field & Francis LLP

(57) ABSTRACT

A synergistic combination of ligands that interact with death domain receptors, and diterpenoid triepoxides is used to increase tumor cell killing by induction of apoptosis. Ligands useful in the invention include TRAIL, TNF-α, analogs thereof, stabilized multimers thereof, mimetics, etc. Of particular interest are combined therapy with the diterpenoid triepoxides triptolide and derivatives and analogs thereof.

10 Claims, 2 Drawing Sheets

OTHER PUBLICATIONS

Snell et al. (1997), "Activity of TNF–Related Apoptosis–Inducing Ligand (TRAIL) in Haematological Malignancies," *British Journal of Hematology,* vol. 99:618–624.

Tengchaisri et al. (1998), "Antitumor Activity of Triptolide Against Cholangiocarcinoma Growth in vitro and in Hamsters," *Cancer Letters,* vol. 133:169–175.

Baker, Stacey J., et al., "Modulation of Life and Death by the TNF Receptor Superfamily," *Oncogene* (1998) vol. 17:3261–3270.

Fanslow, William C., et al., "Structural Characteristics of CD40 Ligand That Determine Biological Function," *Immunology* (1994) vol. 6:267–278.

Gravestein, Loes A., et al., "Tumor Necrosis Factor Receptor Family Members in the Immune System," *Immunology* (1998) vol. 10:423–434.

Griffith, Thomas S., et al., "TRAIL: a Molecule with Multiple Receptors and Control Mechanisms," *Current Opinion in Immunology* (1998) vol. 10:559–563.

Gu, Wen–Zhen, et al., "Isolation, Purification, and Characterization of Immunosuppressive Compounds from Tripterygium:Triptolide and Tripdiolide," *Int. J. Immunopharmac.* (1995) vol. 17(5):351–356.

Pitti, Robert M., et al., "Induction of Apoptosis by Apo–2 Ligand, a New Member of the Tumor Necrosis Factor Cytokine Family," *The Journal of Biological Chemistry* (1996) vol. 271(22):12687–12690.

Shamon, Lisa A., et al., "Evaluation of the Mutagenic Cytotoxic, and Antitumor Potential of Tripolide, a Highly Oxygenated Diterpene Isolated from Tripterygium Wilfordii," *Cancer Letters* (1997) vol. 112:113–117.

Walczak, Henning, et al., "Tumoricial Activity of Tumor Necrosis Factor–Related Apoptosis–Inducing Ligand In Vivo," *Nature Medicine* (Feb. 1999) vol. 5(2):157–163.

Wiley, Steven R., et al., "Identification and Characterization of a New Member of the TNF Family that Induces Apoptosis," *Immunity* (1995) vol. 3:673–682.

Yang, Yili, et al., "Triptolide Induces Apoptotic Death of T Lymphocyte," *Immunopharmacology* (1998) vol. 40:139–149.

* cited by examiner

COMBINED THERAPY OF DITERPENOID TRIEPOXIDES AND DEATH DOMAIN RECEPTOR LIGANDS FOR SYNERGISTIC KILLING OF TUMOR CELLS

CROSS-REFERENCE TO RELATED APPLICATIONS

This application claims the benefit of U.S. Provisional Application No. 60/120,313 filed on Feb. 16, 1999 and U.S. Provisional Application No. 60/149,989 filed on Aug. 20, 1999.

BACKGROUND

The cellular growth of normal tissue is maintained in homeostasis. This balance is determined by cellular proliferation and renewal on one hand, and cell death on the other. Neoplasia can result from aberrant regulation of this homeostasis, through somatic genetic abnormalities that cause cancer initiation and progression. One approach to tumor therapy is to determine agents that act to initiate programmed cell death, or apoptosis. Apoptosis is a form of cell suicide that is critical for differentiation during embryogenesis and regulation of cell numbers. It can also be induced in neoplastic cells, so that they self-destruct. A growing body of evidence suggests that the intracellular "death program" activated during apoptosis is similar in different cell types and conserved during evolution.

Apoptosis involves two essential steps. The Bcl-2 family of proteins that consists of different anti- and pro-apoptotic members is important in the "decision" step of apoptosis. In contrast, the "execution" phase of apoptosis is mediated by the activation of caspases, cysteine proteases that induce cell death via the proteolytic cleavage of substrates vital for cellular homeostasis. Bcl-2-related proteins act upstream from caspases in the cell death pathway.

Tumor necrosis factor (TNF) is the prototypic member of a family of cytokines, which interact with their receptors to carry out diverse functions. Some TNF-receptor family members, termed the "death receptors", which comprise a "death domain", have the unique ability to transmit an intracellular death signal. These receptors include TNF-R1, Fas (CD95), TRAMP (wsl/Apo-3/DR-3), TRAIL-R1 (DR-4) and TRAIL-R2 (DR-5, TRICK2, KILLER). The ligands for these receptors are capable of inducing apoptosis in tumor cells. However, the potential utility of systemically administered TNF, Fas ligand or lymphotoxin has been limited by their acute toxic effects on normal tissues in vivo.

Progress in the treatment of solid tumors has been slow and sporadic. The efficacy of conventional chemotherapy in solid tumors is limited because tumors frequently have mutations in the p53 gene. Also, chemotherapy only kills rapidly dividing cells. Members of the tumor necrosis factor (TNF) family, however, induce apoptosis regardless of the p53 phenotype. Tumor necrosis factor-α (TNF-α), for example, shows broad cytotoxicity against many tumor cell lines but its clinical use is limited because it induces a profound inflammatory response through activation of NF-κB. Moreover, activation of NF-κB inhibits TNF-α-induced apoptosis.

Many cancer cell lines are sensitive to the cytotoxic effects of TRAIL whereas most normal, non-transformed cells are resistant. Walczak et al. (1999) Nature Medicine 5:157–163, fused the receptor-binding region of TRAIL to a leucine zipper motif that favors trimerization. Trimers of leucine zipper TRAIL efficiently killed cultured mammary adenocarcinoma cells but not normal, non-transformed mammary epithelial cells. Systemic administration was able to enhance survival of animals when challenged with this tumor cell line, without detectable adverse effects on viability, tissue integrity, or red and white blood cell counts. The tumoricidal effect of TRAIL was shown to be due to the rapid induction of tumor cell apoptosis.

Strategies to treat tumors with this family of proteins are of great interest. It may be possible to 'sensitize' resistant tumors to apoptosis, for example by modulating the expression or function of FLIP, which blocks the activity of caspases. Other strategies that have been suggested include manipulation of p53 expression. Methods of sensitization may permit the use of lower levels of the proteins, thereby reducing side effects. It may also permit the treatment of otherwise resistant tumors. Approximately 50% of the tumors tested have been resistant to killing by TRAIL (Griffith & Lynch (1998) Curr. Opin. Immunol. 10:559–563).

Relevant Literature

A review of the TNF receptor superfamily may be found in Baker and Reddy (1998) Oncogene 17(25): 3261–70. The tumor necrosis factor receptor (TNFR) superfamily represents a growing family, with over 20 members having been identified thus far in mammalian cells. These proteins share significant homologies in their extracellular ligand binding domains and intracellular effector (death) domains. Death signals seem to be associated with the activation of both the caspase and JUN kinase pathways. Gravestein and Borst (1998) Semin Immunol 10(6): 423–34 also review this receptor superfamily. The use of TRAIL as an anti-tumor agent is discussed in Walczak et al. (1999) Nature Medicine 5:157–163.

Yang et al. (1998) Immunopharmacology 40(2): 139–49 provide evidence that suggests the immunosuppressive agent triptolide inhibits antigen or mitogen-induced T cell proliferation, and induces apoptotic death of T cell hybridomas and peripheral T cells. Shamon et al. (1997) Cancer Lett 112(1): 113–7 evaluate the antitumor potential of triptolide.

The isolation, purification, and characterization of immunosuppressive compounds from tripterygium: triptolide and tripdiolide is reported by Gu et al. (1995) Int J Immunopharmacol 17(5): 351–6.

SUMMARY OF THE INVENTION

Methods are provided for improved killing of tumor cells, by increasing the sensitivity of the cells to apoptosis induced by TNF family death domain ligands (DDL), e.g. TRAIL, TNF, Fas ligand, lymphotoxin, etc. The use of TRAIL or TNF is of particular interest. The tumor cells are contacted with diterpenoid triepoxides, e.g. triptolide, tripdiolide, etc., or prodrugs that convert to such compounds under physiological conditions, either locally or systemically. The killing of the tumor cells by induction of apoptosis through death domain ligands is greatly enhanced by the synergistic action of the diterpenoid and the DDL.

DETAILED DESCRIPTION OF THE EMBODIMENTS

Figure 1:
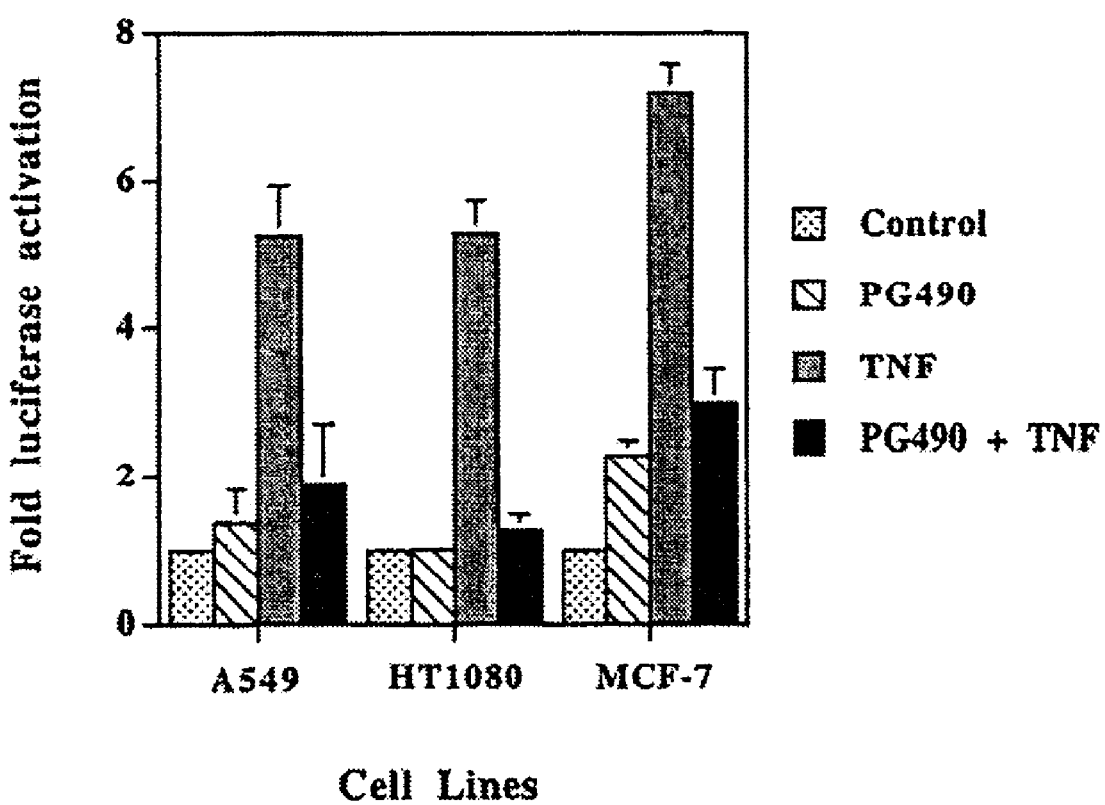
FIG. 1 is a graph depicting PG490 blocking induction of NF-kB transcriptional activity by TNF-α in tumor cell lines. A549, HT1080, and MCF-7 cells that stably express an IgGk NF-kB luciferase reporter gene construct were pretreated with PG490 (20 ng/ml) for 5 h followed by the addition of TNF-α (10 ng/ml) for 6 h. The cells were then harvested for analysis of luciferase activity using equal amounts of protein for each sample. The fold luciferase activation was calculated relative to a normalized value of one given to control (untreated) cells. Data represent the mean luciferase value from triplicates in one experiment, which was used to calculate the mean 6 S.D. from two experiments.

Methods are provided for enhanced killing of tumor cells through the synergistic action of diterpenoid triepoxides, when administered in conjunction with apoptosis inducing ligands of death domain receptors, which include members of the tumor necrosis factor family, such as tumor necrosis factor-α, Fas, lymphotoxin, and TNF-related apoptosis-inducing ligand (TRAIL). Interaction of these ligands with receptors having a death domain causes the responding cell to undergo apoptosis. Although the diterpenoid triepoxides, and the death domain receptor ligands, are able to kill tumor cells when administered alone, the concentrations required for a killing dose may create unacceptable side effects. The potent synergy between the diterpenoids and the death domain ligands allows increased killing at equivalent or lower doses, and can sensitize otherwise resistant cells.

Definitions

It is to be understood that this invention is not limited to the particular methodology, protocols, cell lines, animal species or genera, constructs, and reagents described, as such may vary. It is also to be understood that the terminology used herein is for the purpose of describing particular embodiments only, and is not intended to limit the scope of the present invention which will be limited only by the appended claims.

diterpenoid triepoxide sensitizing agent:

Compounds of interest for use as sensitizing agents include compounds having the structure:

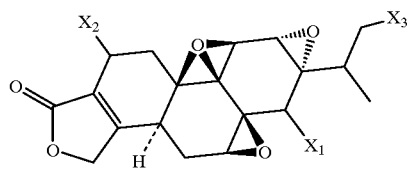

wherein
$X_1$ is OH, =O; or $OR^1$;
$X_2$ and $X_3$ are independently OH, $OR^1$ or H;
$R^1$ is —C(O)Y—Z, wherein Y is a branched or unbranched $C_1$ to $C_6$ alkyl or alkenyl group; and Z is $COOR^2$, $NR^3R^3$, or $+NR^4R^{4'}R^{4''}$, where $R^2$ is a cation; $R^3$ and $R^3$ are independently H or branched or unbranched C, to $C_6$ alkyl, hydroxyalkyl, or alkoxyalkyl, or $R^3$ and $R^3$ taken together form a 5- to 7-member heterocyclic ring whose ring atoms are selected from the group consisting of carbon, nitrogen, oxygen and sulfur, wherein the ring atoms include 2 to 6 carbon atoms, or more nitrogen atoms, and optionally one or more oxygen or sulfur atoms, and wherein the ring is unsubstituted or is substituted with one or more groups selected from $R^5$, $OR^5$, $NR^5R^6$, $SR^5$, $NO_2$, CN, $C(O)R^5$, $C(O)NR^5R^6$, and halogen (fluoro, chloro, bromo, or iodo), where $R^5$ and $R^6$ are independently hydrogen, lower alkyl or lower alkenyl; and $R^4$, $R^{4'}$ and $R^{4''}$ are independently branched or unbranched $C_1$ to $C_6$ alkyl, hydroxyalkyl or alkoxyalkyl. Examples of such molecules may be found in International Patent application WO98/52951, and WO97/31921, herein incorporated by reference.

Compounds of particular interest include triptolide, tripdiolide, triptonide, tripterinin, 16-hydroxytriptolide, triptriolide, and tripchloride; as well as derivatives of triptolide, 16-hydroxytriptolide and tripdiolide (2-hydroxytriptolide) that are derivatized at one or more hydroxyl groups. Such derivatives may be ester derivatives, where the attached ester substituents include one or more amino or carboxylate groups. Prodrugs of particular interest include triptolide succinate sodium salt and triptolide succinate tris(hydroxy-methyl)aminomethane salt.

The compounds of the invention may be prepared from triptolide, tripdiolide, or 16-hydroxytriptolide obtained from the root xylem of the Chinese medicinal plant *Tripterygium wilfordii* or from other known sources. Methods for preparing triptolide and related compounds are known in the art.

Death Domain Receptor Ligand:

Death domain receptor ligands (DDL), as defined herein, refer to compounds, usually polypeptide compounds, that bind to mammalian cell surface receptors comprising a death domain, or homologs or orthologs thereof, and that, by binding so deliver a signal for apoptosis to the cell. The intracellular protein interactions triggered by these receptors can be attributed to binding interactions of the death domain, which is homologous to an approximately 80 amino acid domain near the C-terminus of TNF-R1, and is responsible for signaling cytotoxicity (Huang et al. (1996) *Nature* 384:372–5).

The TNF receptor death domain family includes TNF-R1, Fas (CD95), TRAMP (wsl/Apo-3/DR-3), TRAIL-R1 (DR-4) and TRAIL-R2 (DR-5, TRICK2, KILLER). The extracellular region of the TNF receptor family members carries 2–6 repeats of a cysteine-rich subdomain that has about 25% similarity among various members. The death domain is a homologous domain (about 80 amino acids) in the cytoplasmic regions of Fas and TNFR1. The death domain has a tendency to self-aggregate, and the tertiary structure of the Fas death domain, revealed by heteronuclear multidimensional NMR spectroscopy, shows that the death domain is a novel protein fold consisting of six antiparallel, amphipathic helices. Many charged amino acids are present on the surface, which is probably responsible for mediating the interactions between death domains.

Death domain ligands include proteins that regulate cellular proliferation and differentiation by binding to specific death domain receptors. These ligands include the TNF family, e.g. TNF, lymphotoxin, CD30 ligand, 4-1BB ligand, CD40 ligand, CD27 ligand, and TRAIL (TNF-related apoptosis-inducing ligand), and homologs and analogs thereof. The extracellular region of about 150 amino acids is well conserved (20–25%) among members of the TNF family, while the length and sequence of the cytoplasmic segments differ significantly.

The functional, soluble forms of TNF as well as human FasL exists as trimers. Lymphotoxin β, a member of the TNF family, consists of a heterotrimer of one (lymphotoxin-α, or TNFβ) and two β chains (lymphotoxin-β) on the membrane. X-ray diffraction analyses have indicated that each monomer forms an elongated, antiparallel β-pleated sheet sandwich with a jelly roll topology. Amino acids conserved among members of the TNF family are mainly within the β strands.

Exemplary are ligands of the TRAIL-R1 receptor, and the TNF-R1 receptor. The sequence of the human TRAIL-R1 receptor is provided herein for convenience as SEQ ID NO:2; and the sequence of the human TNF-R1 receptor is provided as SEQ ID NO:3.

The use of the corresponding ligands; TRAIL and TNF-α, are of particular interest. The sequence of human TRAIL is provided herein for convenience as SEQ ID NO:1, the sequence of human TNF-α is provided as SEQ ID NO:4. Identification of non-human homologs is accomplished by conventional screening methods of DNA libraries or biological samples for DNA sequences having a high degree of similarity to known TRAIL sequences.

The sequence of DDL polypeptides may be altered in various ways known in the art to generate targeted changes in sequence. The sequence changes may be substitutions, insertions or deletions, such as deletions of a domain or exon, providing for active peptide fragments of the protein. Other modifications of interest include epitope tagging, e.g. with the FLAG system, HA, etc. Such alterations may be used to alter properties of the protein, by affecting the stability, specificity, etc. An alteration of particular interest stabilizes multimers of TRAIL (for examples see Walczak et al. (1999) *Nature Medicine* 5:157–163; Wiley et al. (1995) *Immunity* 3:673–682; Piti et al. (1996) *J. Biol. Chem.* 271:12687–12690; and Fanslow et al. (1994) *Semin. Immunol.* 6:267–278. The protein may be joined to a wide variety of other oligopeptides or proteins for a variety of purposes. By providing for expression of the subject peptides, various post-expression modifications may be achieved.

Where targeting is desired, the active domain of a DDL may be produced as a fusion protein with an antibody that is specific for a target cell of interest, thereby providing for an antitumor antibody composition. The antibody may be produced as a single chain, instead of the normal multimeric structure. Single chain antibodies are described in Jost et al. (1994) *J.B.C.* 269:26267–73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

DDL DNA sequences may be employed for synthesis of the complete protein, or polypeptide fragments thereof, particularly fragments corresponding to functional domains; binding sites; etc.; and including fusions of the subject polypeptides to other proteins or parts thereof. For expression, an expression cassette may be employed, providing for a transcriptional and translational initiation region, which may be inducible or constitutive, where the coding region is operably linked under the transcriptional control of the transcriptional initiation region, and a transcriptional and translational termination region. Various transcriptional initiation regions may be employed that are functional in the expression host.

The polypeptides may be expressed in prokaryotes or eukaryotes in accordance with conventional ways, depending upon the purpose for expression. For large scale production of the protein, a unicellular organism, such as *E. coli, B. subtilis, S. cerevisiae,* or cells of a higher organism such as vertebrates, particularly mammals, e.g. COS 7 cells, may be used as the expression host cells. In some situations, it may be desirable to express a DDL gene in mammalian cells, where the protein will benefit from native folding and post-translational modifications.

The DDL peptides may also be prepared by synthesis. Various commercial synthetic apparatuses are available, for example automated synthesizers by Applied Biosystems Inc., Foster City, Calif., Beckman, etc. By using synthesizers, naturally occurring amino acids may be substituted with unnatural amino acids, particularly diastereoisomers, side chains having different lengths or functionalities, and the like. The particular sequence and the manner of preparation will be determined by convenience, economics, purity required, and the like.

Other molecules that interact with the death domain receptors may be used in the subject methods. Such ligands will specifically bind to the extracellular domain of the receptor, and compete with the cognate ligand for binding. Ligands will also activate signaling through the death domain to activate apoptosis. Candidate ligands are screened for their ability to meet this criteria. Assays to determine affinity and specificity of binding are known in the art, including competitive and non-competitive assays. Assays of interest include ELISA, RIA, flow cytometry, etc. Binding assays may use purified or semi-purified protein, or alternatively may use cells that express a DDL, e.g. cells transfected with an expression construct for a DDL, etc. As an example of a binding assay, purified receptor protein is bound to an insoluble support, e.g. microtiter plate, magnetic beads, etc. The candidate ligand and soluble, labeled DDL are added to the cells, and the unbound components are then washed off The ability of the ligand to compete for receptor binding is determined by quantitation of bound, labeled ligand. A functional assay that detects apoptosis may be used for confirmation.

Suitable ligands in addition to TRAIL, TNF-α, and variants thereof, include peptides, small organic molecules, peptidomimetics, antibodies, or the like. Antibodies may be polyclonal or monoclonal; intact or truncated, e.g. $F(ab')_2$, Fab, Fv; xenogeneic, allogeneic, syngeneic, or modified forms thereof, e.g. humanized, chimeric, etc.

In many cases, the ligand will be an polypeptide, e.g. TRAIL, TNF-α, a specifically binding antibody thereto or fragment thereof, etc., but other molecules that provide relatively high specificity and affinity may also be employed. Combinatorial libraries provide compounds other than oligopeptides that have the necessary binding characteristics. Generally, the affinity will be at least about 10–6, more usually about $10^{-8}$ M, i.e. binding affinities normally observed with specific monoclonal antibodies.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl, sulfhydryl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives; structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

Suitable antibodies for use as ligands are obtained by immunizing a host animal with peptides comprising all or a portion of a DDL. Suitable host animals include mouse, rat sheep, goat, hamster, rabbit, etc. The origin of the protein immunogen may be mouse, human, rat, monkey etc. The host animal will generally be a different species than the immunogen, e.g. mouse TRAIL used to immunize hamsters, human TNF-α to immunize mice, etc. Methods to generate monoclonal antibodies are well known in the art and need not be further elaborated.

Susceptible tumors:

The host, or patient, may be from any mammalian species, e.g. primate sp., particularly humans; rodents, including mice, rats and hamsters; rabbits; equines, bovines, canines, felines; etc. Animal models are of interest for experimental investigations, providing a model for treatment of human disease.

Tumors known susceptible to induction of apoptosis include carcinomas, e.g. colon, prostate, breast, melanoma, ductal, endometrial, stomach, dysplastic oral mucosa, invasive oral cancer, non-small cell lung carcinoma, transitional and squamous cell urinary carcinoma, etc.; neurological malignancies, e.g. neuroblastoma, gliomas, etc.; hematological malignancies, e.g. childhood acute leukaemia, non-Hodgkin's lymphomas, chronic lymphocytic leukaemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; and the like.

Some cancers of particular interest include non-small cell lung carcinoma. Non-small cell lung cancer (NSCLC) is made up of three general subtypes of lung cancer. Epidermoid carcinoma (also called squamous cell carcinoma) usually starts in one of the larger bronchial tubes and grows relatively slowly. The size of these tumors can range from very small to quite large. Adenocarcinoma starts growing near the outside surface of the lung and may vary in both size and growth rate. Some slowly growing adenocarcinomas are described as alveolar cell cancer. Large cell carcinoma starts near the surface of the lung, grows rapidly, and the growth is usually fairly large when diagnosed. Other less common forms of lung cancer are carcinoid, cylindroma, mucoepidermoid, and malignant mesothelioma.

The majority of breast cancers are adenocarcinomas subtypes. Ductal carcinoma in situ is the most common type of noninvasive breast cancer. In DCIS, the malignant cells have not metastasized through the walls of the ducts into the fatty tissue of the breast. Infiltrating (or invasive) ductal carcinoma (IDC) has metastasized through the wall of the duct and invaded the fatty tissue of the breast. Infiltrating (or invasive) lobular carcinoma (ILC) is similar to IDC, in that it has the potential metastasize elsewhere in the body. About 10% to 15% of invasive breast cancers are invasive lobular carcinomas.

Melanoma is a malignant tumor of melanocytes. Although most melanomas arise in the skin, they also may arise from mucosal surfaces or at other sites to which neural crest cells migrate. Melanoma occurs predominantly in adults, and more than half of the cases arise in apparently normal areas of the skin. Prognosis is affected by clinical and histological factors and by anatomic location of the lesion. Thickness and/or level of invasion of the melanoma, mitotic index, tumor infiltrating lymphocytes, and ulceration or bleeding at the primary site affect the prognosis. Clinical staging is based on whether the tumor has spread to regional lymph nodes or distant sites. For disease clinically confined to the primary site, the greater the thickness and depth of local invasion of the melanoma, the higher the chance of lymph node metastases and the worse the prognosis. Melanoma can spread by local extension (through lymphatics) and/or by hematogenous routes to distant sites. Any organ may be involved by metastases, but lungs and liver are common sites.

Pharmaceutical Formulations:

The compounds of this invention can be incorporated into a variety of formulations for therapeutic administration. More particularly, the compounds of the present invention can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The active agent may be systemic after administration or may be localized by the use of regional administration, intramural administration, or use of an implant that acts to retain the active dose at the site of implantation.

In pharmaceutical dosage forms, the compounds may be administered in the form of their pharmaceutically acceptable salts. They may also be used in appropriate association with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing sensitizer is placed in proximity to the site of the tumor, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms of the present invention depend on the particular compound employed and the effect to be achieved, and the pharmacodynamics associated with each compound in the host.

Pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosage:

The combined used of diterpenoid triepoxides and DDL compounds has the advantages that the required dosages for the individual drugs is lower, and the effect of the different drugs complementary. Depending on the patient and condition being treated and on the administration route, the diterpenoid triepoxides will generally be administered in dosages of 0.001 mg to 5 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus for example oral dosages in the rat may be ten times the injection dose. The dosage for the death domain receptor ligand will vary substantially with the compound. For example, it has been found that dosages of up to 5 mg/kg are tolerated of TRAIL polypeptides in rodents (Walczak et al., supra.), although dosages in humans may be substantially lower, e.g. from about 0.05 mg/kg to about 0.5 mg/kg/day. Higher doses may be used for localized routes of delivery.

A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For use in the subject methods, the DDL and diterpenoid triepoxides may be formulated with other pharmaceutically active agents, particularly other anti-metastatic, anti-tumor or anti-angiogenic agents. Angiostatic compounds of interest include angiostatin, endostatin, carboxy terminal peptides of collagen alpha (XV), etc. Cytotoxic and cytostatic agents of interest include adriamycin, alkeran, Ara-C, BICNU, busulfan, CNNU, cisplatinum, cytoxan, daunorubicin, DTIC, 5-FU, hydrea, ifosfamide, methotrexate, mithramycin, mitomycin, mitoxantrone, nitrogen mustard, velban, vincristine, vinblastine, VP-16, carboplatinum, fludarabine, gemcitabine, idarubicin, irinotecan, leustatin, navelbine, taxol, taxotere, topotecan, etc.

Methods of Use

A combined therapy of diterpenoid triepoxide compounds and death domain ligand is administered to a host suffering from a susceptible tumor. Administration may be topical, localized or systemic, depending on the specific disease. The compounds are administered at a combined effective dosage that over a suitable period of time substantially reduces the tumor cell burden, while minimizing any side-effects, usually killing at least about 25% of the tumor cells present, more usually at least about 50% killing, and may be about 90% or greater of the tumor cells present. It is contemplated that the composition will be obtained and used under the guidance of a physician for in vivo use.

To provide the synergistic effect of a combined therapy, the DDL and the diterpenoid triepoxide active agents can be delivered together or separately, and simultaneously or at different times within the day. In one embodiment of the invention, the diterpenoid triepoxide compounds are delivered prior to administration of the DDL.

The susceptibility of a particular tumor cell to killing with the combined therapy may be determined by in vitro testing, as detailed in the experimental section. Typically a culture of the tumor cell is combined with a combination of a DDL and a diterpenoid triepoxide at varying concentrations for a period of time sufficient to allow the active agents to induce apoptosis, usually between about one hour and one week. For in vitro testing, cultured cells from a biopsy sample of the tumor may be used. The viable cells left after treatment are then counted.

The dose will vary depending on the specific cytotoxic agent utilized, type of tumor, patient status, etc., at a dose sufficient to substantially ablate the tumor cell population, while maintaining patient viability. In some cases therapy may be combined with stem cell replacement therapy to reconstitute the patient hematopoietic function. Treatment will generally be continued until there is a substantial reduction, e.g. at least about 50%, decrease in the tumor burden, and may be continued until there are essentially no tumor cells detected in the body.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the array" includes reference to one or more arrays and equivalents thereof known to those skilled in the art, and so forth. All technical and scientific terms used herein have the same meaning as commonly understood to one of ordinary skill in the art to which this invention belongs unless clearly indicated otherwise.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

EXAMPLE 1

Synergistic Killing of Tumor Cells with TRAIL and Triptolide

Members of the tumor necrosis factor family such as tumor necrosis factor-α, Fas and TNF-related apoptosis-inducing ligand (TRAIL), also known as Apo2L, induced programmed cell death, apoptosis, in tumor cells. Recent studies show that TRAIL is more cytotoxic than TNF-α and Fas in solid tumor cell lines and TRAIL is less toxic than Fas and TNF-α to normal cells. There are, however, several tumor cell lines which are resistant or relatively resistant to the cytotoxic action of TRAIL.

We have found that PG490, which contains purified triptolide, induces apoptosis in many solid tumor cell lines. Additionally, the combination of PG490 and chemotherapy is more cytotoxic than each alone. Potent synergy was observed between PG490 plus TNF-α and PG490 plus TRAIL. The combination of PG490 plus TRAIL induces apoptosis in greater than 80–99% of cells in all solid tumor cell lines tested. This combination is more effective than chemotherapy alone or chemotherapy plus TRAIL. Even cell lines that are relatively resistant to PG490 or TRAIL alone, such as ME180 cervical cancer cells, are dramatically senstive to the combination of PG490 plus TRAIL with cell death in greater than 80% of cells.

Materials and Methods
Source of triptolide.
PG490 (triptolide, MW 360) was obtained from Pharmagenesis (Palo Alto, Calif.). The material was composed of white to off-white crystals, had a melting point of 226–240° C., conformed to a standard triptolide preparation by Proton Nuclear Magentic Resonance (5), and was 97% pure by reverse phase HPLC evaluation using acetonitrile:methanol:water (18:9:73; J. Fidler and R. L. Jin, Pharmagenesis, private communication)

Cell Lines.
A549 and H1299 (non-small cell lung cancer), ME180 (cervical carcinoma) and MDA-MB231 (mammary adenocarcinoma) cell lines were purchased from ATCC. Cells were cultured in the appropriate media with 10% FCS supplemented with L-glutamine, penicillin and streptomycin.

Expression and Purification of Purified TRAIL.
TRAIL codons 95–285 were amplified by polymerase chain reaction and subcloned into a pQE-9 (Qiagen, Santa Clarita, Calif.) bacterial expression vector downstream of a 6X-Histidine tag. TRAIL was purified by Nickel affinity chromatography according to the manufacturer's protocol. The purity of TRAIL was confirmed by Coomassie blue staining.

Cell death reagents and assays.
Cell viability was measured by an MTT assay. Briefly, untreated cells or cells treated with PG490 (5–100 ng/ml) and/or TRAIL (10–1000 ng/ml) in a 96-well plate were harvested at 48 h followed by the addition of 3-(4,5-dimethylthiazol-2-yl)-2,5-diphenyltetrazolium bromide (MTT) to the cells. Cells were then solubilized with 0.0N acidified $CH_3Cl$—HCL. The 96-well plate was read at a wavelength of 590 nm on an iEMS Labsystems plate reader. Induction of cell death by TRAIL, PG490 and PG490 plus TRAIL was confirmed as apoptotic by Annexin staining followed by FACS analysis.

The combination of triptolide and TRAIL induced apoptosis in greater than 95% of cells in diverse solid tumor cell lines, including lung, breast and sarcoma cell lines. For example, in the non-small cell lung carcinoma H1299, triptolide or TRAIL alone induce apoptosis in less than 50% of cells, but the combination treatment induced apoptosis in greater than 95% of the cells.

TABLE 1

| | % Viable Cells | | | |
|---|---|---|---|---|
| Cell lines | A549 | ME180 | H1299 | MDA-MB 231 |
| PG490 20 ng/ml | 60.7 | 84.8 | 46.0 | 62.9 |
| TRAIL 100 ng/ml | 55.5 | 80.0 | 55.1 | 54.4 |
| PG490 + TRAIL | 5.6 | 15.2 | 3.4 | 2.1 |

Maximal cytotoxicity was achieved with a combination of triptolide and TRAIL when cells were pre-treated with triptolide for 2–5 hours prior to the addition of TRAIL. This combination was effective in cells that lack p53, such as the H1299 cell line. The combination therapy was more cytotoxic in these cells lines than chemotherapy alone (carboplatinum, doxorubicin or taxol), or chemotherapy in combination with TRAIL.

TRAIL at 100 ng/ml induced a four fold increase in NF-κB transcriptional activity in A549 (p53 wild type) and a two fold increase in NCl-H-1299 (p53 null) nonsmall cell lung cancer cell lines. Triptolide inhibited TRAIL-induced NF-κB activation by 90–95%. The cytotoxicity of TRAIL alone in both cell lines was less than 30% but increased to 80–95% in combination with triptolide. Pretreatment with MG132, a proteasome inhibitor that inhibits NF-κB, also sensitized A549 and H1299 cells to TRAIL0induced apoptosis.

The data show that triptolide and TRAIL act in synergy to induce appoptosis in greater than 80% of cells in several diverse solid tumor cell lines.

EXAMPLE 2

Synergism of Triptolide and TNF-α

Activation of NF-kB suppresses apoptosis in tumor cells, and tumor cells are sensitized to TNF-α-induced apoptosis through inhibition of NF-kB. The data presented herein demonstrates that purified triptolide sensitizes several solid tumor cell lines to TNF-α-induced apoptosis through inhibition of NF-kB. Interestingly, triptolide inhibited transcriptional activation of NF-kB but not DNA binding of NF-kB. Also, triptolide blocked induction of c-IAP2 and c-IAP1 by TNF-α. The ability of triptolide to augment TNF-α-induced cytotoxicity while simultaneously inhibiting activation of NF-kB may enhance the cytotoxic potential of TNF-α and limit its proinflammatory effects in vivo.

MATERIALS AND METHODS

Source of Triptolide.

PG490 (triptolide, molecular weight, 360) was obtained from Pharmagenesis (Palo Alto, Calif.). The material was composed of white to off-white crystals, had a melting point of 226–240° C., conformed to a standard triptolide preparation by proton nuclear magnetic resonance, and was 97% pure by reverse phase high pressure liquid chromatography evaluation using acetonitrile:methanol:water (18:9:73).

Cells and Transfections.

A549 (nonsmall cell lung cancer) and HT1080 (fibrosarcoma) cell lines were purchased from ATCC. An MCF-7 (breast cancer) cell subline was provided by Dr. Ron Weigel (Stanford University). Cells were cultured in the appropriate media with 10% fetal calf serum supplemented with L-glutamine, penicillin, and streptomycin. TNF-α was obtained from R&D Systems (Minneapolis, MN) and phorbol myristyl acetate from Sigma. Cells were left untreated or stimulated with PG490 (20 ng/ml) and/or TNF-α (10 ng/ml), and 6 h after the addition of TNF-α, cells were harvested for analysis of luciferase activity according to the manufacturer's protocol (Promega Corp., Madison, Wis.). In experiments with PG490 and TNF-α, cells were pretreated with PG490 for 4 h before the addition of TNF-α. Luciferase activity was measured in samples that contained equal protein concentration with a Luminometer (Analytical Luminescence Laboratory, San Diego, Calif.).

Plasmids.

An oligonucleotide containing the IgGk-NF-kB site (sequence 5'-GGGGACTTTCC-3') was placed upstream of a minimal interleukin-8 promoter (position 267 to 144) in a luciferase reporter gene construct and stably transfected into A549, HT180, and MCF-7 cells. Resistant clones were pooled after selection in 400–600 mg/ml G418. The IkBα super-repressor construct is described in Brockman et al. (1995) *Mol. Cell. Biol.* 15:2809–2818. The Gal4 DNA binding domain (amino acids 1–147), Gal4-p65 TA1, and Gal4-p65 TA2 constructs are described in Schmitz et al. (1995) *J. Biol. Chem.* 270:15576–15584. The Gal4-luciferase construct contains 5X Gal4 binding sites upstream of a minimal interleukin-2 promoter with a luciferase reporter gene.

Cell Death Reagents and Assays.

Cell viability was measured by a 3-(4,5-dimethyl thiazol-2-yl)-2,5-diphenyl tetrazolium bromide assay. Briefly, untreated cells or cells treated with PG490 and/or TNF-α in a 96-well plate were harvested at the indicated times followed by the addition of 3-(4,5-dimethyl thiazol-2-yl)-2,5-diphenyl tetrazolium bromide to the cells. Cells were then solubilized with 0.1 N acidified $CH_3Cl$—HCl. The 96-well plate was read at a wavelength of 590 nm on an iEMS Labsystems plate reader. Induction of cell death by TNF-α, PG490, and PG490 plus TNF-α was confirmed as apoptotic by Annexin staining followed by fluorescence-activated cell sorter analysis as described previously in Wen et al. (1997) *J. Biol. Chem.* 272:26056–26061.

Electrophoretic Mobility Shift Assay.

A549, HT1080, and MCF-7 cells were treated under the following conditions: (1) unstimulated; (2) PG490 (20 ng/ml) for 5 h; (3) TNF-α (10 ng/ml) for 1 h; (4) PG490 pretreatment for 4 h followed by TNF-α for 1 h. Nuclear extracts were prepared using a protocol described by Lee et al. (1988) *Gene Anal. Tech.* 5:22–31. The electrophoretic mobility shift assay was performed as described previously using a Klenow-labeled $^{32}$P-IgG NF-kB site as a probe (Rosen et al. (1994) *J. Biol. Chem.* 269:15652–15660). Supershift studies were done with a p65 monoclonal antibody (Santa Cruz Biochemical, Santa Cruz, Calif.).

Coimmunoprecipitation Studies.

To detect the association of p65 with cAMP response element-binding protein (CBP) in untreated A549 cells or A549 cells treated with PG490 (20 ng/ml) and/or TNF-α (10 ng/ml), cellular protein was extracted for immunoprecipitation as described previously (Wen et al. (1997), supra.) Cellular protein was immunoprecipitated with a CBP mouse polyclonal antibody (Santa Cruz Biotechnology) followed by Western blot analysis with a p65 mouse monoclonal antibody (BI-OMOL, Plymouth Meeting, Pa.) using a Western blot protocol described previously (Wen et al. (1997), supra.) Northern Blot Analysis and RT-PCR. RNA was harvested from A549 cells with RNA STAT-60, a solution containing guanidine isothiocyanate and phenol (Tel-Test "B", Friendswood, Tex.), and Northern blot analysis was done as described previously (Wen et al. (1997), supra.) The c-IAP1 and c-IAP2 cDNAs were provided by Tularik, South San Francisco, Calif.). A plasmid that contains a 115-base pair fragment from the 28 S ribosomal RNA cDNA was purchased from Ambion (Austin, Tex.), excised with Kpnl and Xbal and used in Northern blot analysis to demonstrate equal loading of RNA. For RT-PCR RNA was isolated from MCF-7 cells using RNA STA-60 and subjected to RT-PCR with oligonucleotide primers for c-IAP2.

RESULTS

PG490 Induces Apoptosis in Solid Tumor Cells and Sensitizes Tumor Cells to TNF-α-induced Apoptosis.

Compounds were sought that would sensitize tumor cells to TNF-α through inhibition of NF-kB. PG490 (triptolide) is a diterpene epoxide derived from a traditional Chinese herb that possesses potent immunosuppressive and anticancer activity in vitro. It was examined whether PG490 inhibits TNF-α-mediated activation of NF-kB and sensitizes tumor cells to TNF-α-induced apoptosis.

PG490 alone decreased cell viability by 40–70% of cells in several solid tumor cell lines at dosages between 520 ng/ml (Table I). Cell death was confirmed as apoptotic by Annexin staining followed by fluorescence-activated cell sorter analysis. Cell death was maximal at 48 h after the addition of PG490. Several tumor cells lines such as HT1080 cells are resistant to TNF-α because of NF-kB activation following stimulation with TNF-α. It was also found that A549 lung cancer cells are resistant to TNF-α-induced apoptosis (Table I). MCF-7 breast cancer cells show intermediate sensitivity to TNF-α with TNF-α inducing cell death in approximately 30% of cells. PG490 alone (20 ng/ml) induced cell death in approximately 30% of cells in the A549 cell line but the combination of PG490 and TNF-α-induced cell death in over 80% of cells. In contrast to A549 cells, PG490 alone (20 ng/ml) induced cell death in 70–75% of cells in the MCF-7 cell line and 50–55% of cells in the HT1080 cell line. PG490 at a concentration of 5 ng/ml induced cell death in approximately 35% of MCF-7 cells and the combination of PG490 (5 ng/ml) plus TNF-α induced cell death in approximately 80% of MCF-7 cells. In HT1080 cells the combination of PG490 (20 ng/ml) plus TNF-α induced cell death in more than 99% of cells.

TABLE I

Effect of PG490 and TNF-a on tumor cell viability

| Treatment | Cell Line | | |
|---|---|---|---|
|  | A549 | HT1080 | MCF-7 |
| PG490 5 ng/ml | 87.9 ± 7.0 | 86.6 ± 6.5 | 63.9 ± 9.9 |
| PG490 20 ng/ml | 67.5 ± 5.4 | 46.4 ± 4.8 | 30.5 ± 9.3 |
| TNF-α 10 ng/ml | 93.4 ± 1.3 | 94.7 ± 3.5 | 67.8 ± 6.5 |
| PG490 5 ng/ml + TNF-α 10 ng/ml | 79.6 ± 9.1 | 71.2 ± 2.9 | 21.4 ± 3.0 |
| PG490 20 ng/ml + TNF-α 10 ng/ml | 17.4 ± 10.4 | 0.2 ± 0.3 | 15.6 ± 4.1 |

Cell lines were incubated with PG490 and/or TNF-αfor 48 h followed by analysis of cell viability by an MTT assay. In experiments with PG490 plus TNF-α cells were pretreated with PG490 for 4 h before the addition of TNF-α. Values are mean of three experiments 6 S.D.

It was examined whether PG490 inhibits TNF-α-mediated activation of NF-kB in HT1080, A549, and MCF-7 cells. It was found that PG490 inhibited TNF-α-induced activation of an IgGk NF-kB luciferase reporter gene construct in all three cell lines but PG490 did not affect basal NF-kB activity (FIG. 1). PG490 alone did not affect basal NF-kB activity in A549 and HT1080 cells but it slightly induced NF-kB transcriptional activity in MCF-7 cells. It was also observed that PG490 inhibits expression of the IkBa protein in MCF-7 cells leading to increased binding of NF-kB, which may explain the increase in NF-kB transcriptional activity.

PG490 Does not Inhibit DNA Binding of NF-kB.

To determine whether PG490 inhibits activation of NF-kB through the inhibition of DNA binding of NF-kB, the effect of PG490 on TNF-α-induced binding of NF-kB was examined by electrophoretic mobility shift assay. TNF-α induced binding of NF-kB in A549 cells, and an antibody to p65 (Rel A) (Santa Cruz Biotechnology) supershifted the complex demonstrating that p65 is part of the NF-kB complex induced by TNF-α. PG490 did not affect the intensity of the NF-kB complex induced by TNF-α or its migration in A549 cells. PG490 alone did not induce binding of NF-kB; antibodies to p65 also supershifted a specific complex in PG490 plus TNF-α-treated cells. PG490 also did not affect TNF-α-induced binding of NF-kB in HT1080 or MCF-7 cells. These results suggest that PG490 inhibits transactivation but not DNA binding of NF-kB.

PG490 Inhibits Transcriptional Activation of p65.

Recent studies have shown that phosphorylation of p65 is important for transcriptional activation of NF-kB. Lipopolysaccharide induces phosphorylation of p65 on serine 276, which increases p65-mediated transactivation. TNF-α induces phosphorylation of p65 on serine 529, in the C-terminal region of p65. Inducible phosphorylation of p65 does not affect nuclear translocation or DNA binding activity of NF-kB but it increases transcriptional activity.

Figure 2:
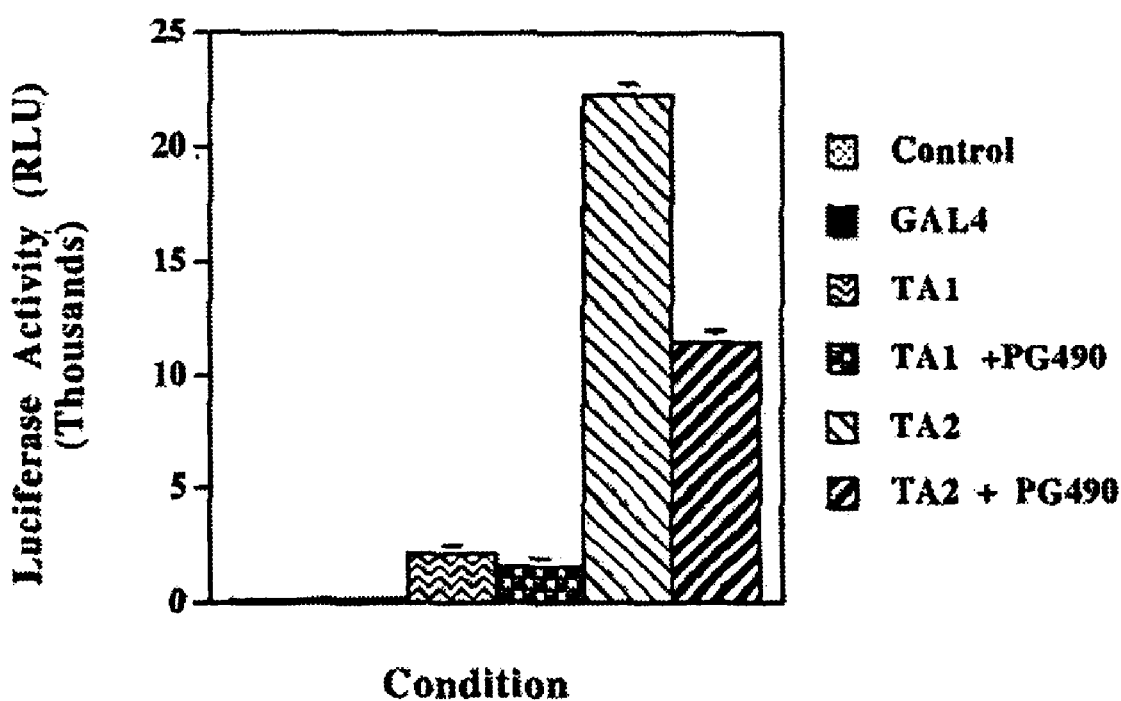
FIG. 2 is a graph depicting PG490 inhibition of the transcriptional activity of p65. A vector encoding a fusion protein between the DNA binding domain of Gal4 and either the TA1 (Gal4-p65 TA1) or TA2 (GAL4-p65 TA2, which contains TA1) activation domains of p65 or Gal4 was cotransfected with a 5XGal4-luciferase reporter gene construct into A549 cells and placed in 0.1% serum-containing medium 3 h after transfection. After 36 h, cells were pretreated with PG490 (20 ng/ml) for 5 h followed by the addition of TNF-α (10 ng/ml) for 6 h. Cells were then harvested for analysis of luciferase activity using equal amounts of protein.

It was tested whether PG490 would inhibit transactivation of p65. A plasmid encoding a fusion protein of the transactivating domains of p65, Gal4-p65 521–551 (Gal4-p65 TA1) or Gal4-p65 268–551 (Gal4-p65 TA2), with the DNA binding domain of the yeast transcription factor Gal4, was transfected into A549 cells along with a luciferase reporter containing upstream Gal4 binding sites. The TA1 domain is contained within the TA2 construct. It was found that PG490 blocked transcriptional activity of the TA1 domain of p65 by 20–25% and of the TA2 domain by over 50% (FIG. 2). TNF-α did not stimulate transcriptional activity of the TA1 or TA2 domain even when the A549 cells were grown in medium containing 0.1% serum, which reduced basal NF-kB activity. This lack of response to TNF-α may be explained by the observation that A549 cells contain significant basal NF-kB activity. Nonetheless, PG490 significantly blocked transcriptional activity of the transactivating domains of p65.

PG490 Does not Affect the Interaction of p65 with CBP.

Recent studies suggest that CBP/p300 are transcriptional co-activators of the p65 subunit of NF-kB. The interaction of p65 with CBP/p300 requires phosphorylation of p65 at serine 276. p65 then interacts with CBP/p300 in the nucleus, which enhances NF-kB-dependent transcription. It was examined whether PG490 inhibits transactivation of NF-kB by blocking the interaction of p65 with CBP/p300, and found that p65 associated with CBP/p300 in unstimulated A549 cells, and this complex was induced by TNF-α. PG490, however, did not affect the intensity or migration of the p65*CBP complex in TNF-α-treated A549 cells. PG490 alone, in fact, increased the association of CBP with p65 in unstimulated A549 cells.

PG490 Suppresses the Induction of c-IAP2 and C-IAP1 by TNF-α.

Recent studies demonstrate that members of the inhibitor of apoptosis family such as c-IAP1 (hiap-2) and c-IAP2 (hiap-1) suppress TNF-α-mediated cell death. It was tested whether PG490 would block induction of c-IAP2 and c-IAP1 by TNF-α. TNF-α induced a 6-fold increase in c-IAP2 mRNA and a 4-fold increase in c-IAP1 mRNA in A549 cells, which was almost completely blocked by PG490. TNF-α also induced a 4-fold increase in c-IAP2 mRNA in MCF-7 cells, which was blocked by PG490. These results suggest that PG490 sensitizes tumor cells to TNF-α-induced apoptosis, at least in part, by suppressing the induction of c-IAP2 and c-IAP1.

Over 50–70% of solid tumors harbor mutations in p53, which confers relative chemoresistance. TNF family members such as TNF-α, Fas, and TNF-related apoptosis-inducing ligand, also known as Apo2L, induce apoptosis in tumor cells regardless of the p53 phenotype. Unfortunately, TNF-α-induced apoptosis is limited by activation of NF-kB. Additionally, activation of NF-kB induces the release of proinflammatory cytokines, which damage the host.

PG490 (triptolide) is an oxygenated diterpene derived from a traditional Chinese herb that has been used as an immunosuppressant in China for the treatment of rheumatoid arthritis. There are also studies that show PG490 is cytotoxic in leukemia and breast cancer cell lines. It is shown here that PG490 cooperates with TNF-α to induce apoptosis in diverse solid tumor cell lines.

PG490 alone induces apoptosis in 30–70% of cells in the A549, HT1080, and MCF-7 cell lines. Other tumor cell lines are even more sensitive to PG490-induced apoptosis. PG490 almost completely suppresses TNF-α-induced activation of NF-kB and sensitizes tumor cell lines to TNF-α-induced apoptosis. Recent studies suggest that c-IAP1 (hiap-2) and c-IAP2 (hiap-1) mediate, at least in part, the resistance of some tumor cells to TNF-α-induced apoptosis. The present data show that TNF-α induced c-IAP1 and c-IAP2, and that PG490 blocked TNF-α-mediated induction of c-IAP2 and c-IAP1.

PG490 did not affect the DNA binding of NF-kB but it blocked transactivation of NF-kB. It is shown that PG490 inhibits transactivation of both the TA1 and TA2 regions of p65 (FIG. 2). PG490 did not, however, affect the interaction of p65 with CBP in TNF-α treated cells. The results suggest that PG490 may block the phosphorylation of NF-kB at Ser-529 and/or the association of p65 with a transcriptional cofactor in the nucleus.

What is claimed is:

1. A method for enhanced killing of tumor cells, the method comprising:
   contacting a susceptible tumor cell with a synergistic combination of a death domain receptor ligand; and a diterpenoid triepoxide having the structure:

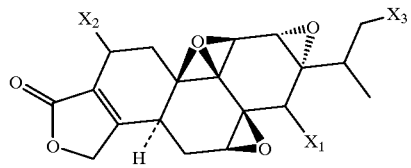

wherein
$X_1$ is OH, =O; or $OR^1$;
$X_2$ and $X_3$ are independently OH, $OR^1$ or H;
$R^1$ is —C(O)—Y—Z, wherein Y is a branched or unbranched $C_1$ to $C_5$ alkyl or alkenyl group; and Z is $COOR^2$, $NR^3R^3$, or $+NR^4R^4R^4$, where $R^2$ is a cation; $R^3$ and $R^3$ are independently H or branched or unbranched $C_1$ to $C_6$ alkyl, hydroxyalkyl, or alkoxyalkyl, or $R^3$ and $R^3$ taken together form a 5- to 7-member heterocyclic ring whose ring atoms are selected from the group consisting of carbon, nitrogen, oxygen and sulfur, wherein the ring atoms include 2 to 6 carbon atoms, or more nitrogen atoms, and optionally one or more oxygen or sulfur atoms, and wherein the ring is unsubstituted or is substituted with one or more groups selected from $R^5$, $OR^5$, $NR^5R^6$, $SR^5$, $NO_2$, CN, $C(O)R^5$, $C(O)NR^5R^6$, and halogen (fluoro, chloro, bromo, or iodo), where $R^5$ and $R^6$ are independently hydrogen, lower alkyl or lower alkenyl; and $R^4$, $R^4$ and $R^4$ are independently branched or unbranched $C_1$ to $C_6$ alkyl, hydroxyalkyl or alkoxyalkyl; in a combined dosage effective to kill at least about 50% of said tumor cells.

2. The method of claim 1, wherein said diterpenoid triepoxide is selected from the group consisting of triptolide, tripdiolide, 16-hydroxytriptolide; triptolide succinate, an ester derivative of triptolide, an ester derivative of tripdiolide, and an ester derivative of 16-hydroxytriptolide.

3. The method of claim 1, wherein said death domain receptor ligand is human TRAIL polypeptide or an active fragment thereof.

4. The method of claim 3, wherein said TRAIL polypeptide is a soluble, stabilized multimer.

5. The method of claim 1, wherein said death domain receptor ligands is human TNF-α polypeptide or an active fragment thereof.

6. The method of claim 1, wherein said tumor is a human tumor.

7. The method of claim 6, wherein said tumor is a solid tumor.

8. The method of claim 6, wherein said tumor is a carcinoma.

9. The method of claim 6, wherein said tumor is a mammary adenocarcinoma.

10. The method of claim 6 wherein said tumor is a non-small cell lung carcinoma.

* * * * *

UNITED STATES PATENT AND TRADEMARK OFFICE
CERTIFICATE OF CORRECTION

PATENT NO. : 6,329,148 B1
DATED : December 11, 2001
INVENTOR(S) : Rosen, Glenn D. et al.

It is certified that error appears in the above-identified patent and that said Letters Patent is hereby corrected as shown below:

Column 12,
Line 31, please correct as follows:
-- (MTT) to the cells. Cells were then solubilized with 0.1N --

Column 13,
Line 6, please correct as follows:
-- Induce apoptosis in greater that 80% of cells in several --

Column 15,
Line 18, please correct as follows:
-- TNF-a induced cell death in more that 99% of cells. --
Line 44, please correct as follows:
-- IkBα protein in MCF-7 cells leading to increased binding of --
Line 64, please correct as follows:
-- independently H or branched or unbranched $C_1$, to $C_6$ --

Signed and Sealed this

Fourteenth Day of January, 2003

JAMES E. ROGAN
*Director of the United States Patent and Trademark Office*

SEQUENCE LISTING

<160> NUMBER OF SEQ ID NOS: 4

<210> SEQ ID NO 1
<211> LENGTH: 1769
<212> TYPE: DNA
<213> ORGANISM: H. sapiens
<220> FEATURE:
<221> NAME/KEY: CDS
<222> LOCATION: (88)...(933)
<223> OTHER INFORMATION: Human TRAIL Coding Sequence

<400> SEQUENCE: 1

```
cctcactgac tataaaagaa tagagaagga agggcttcag tgaccggctg cctggctgac        60
ttacagcagt cagactctga caggatc atg gct atg atg gag gtc cag ggg gga      114
                                Met Ala Met Met Glu Val Gln Gly Gly
                                 1               5 ccc agc ctg gga cag acc tgc gtg ctg atc gtg atc ttc aca gtg ctc        162
Pro Ser Leu Gly Gln Thr Cys Val Leu Ile Val Ile Phe Thr Val Leu
 10              15                  20                  25 ctg cag tct ctc tgt gtg gct gta act tac gtg tac ttt acc aac gag        210
Leu Gln Ser Leu Cys Val Ala Val Thr Tyr Val Tyr Phe Thr Asn Glu
                 30                  35                  40 ctg aag cag atg cag gac aag tac tcc aaa agt ggc att gct tgt ttc        258
Leu Lys Gln Met Gln Asp Lys Tyr Ser Lys Ser Gly Ile Ala Cys Phe
             45                  50                  55 tta aaa gaa gat gac agt tat tgg gac ccc aat gac gaa gag agt atg        306
Leu Lys Glu Asp Asp Ser Tyr Trp Asp Pro Asn Asp Glu Glu Ser Met
         60                  65                  70 aac agc ccc tgc tgg caa gtc aag tgg caa ctc cgt cag ctc gtt aga        354
Asn Ser Pro Cys Trp Gln Val Lys Trp Gln Leu Arg Gln Leu Val Arg
     75                  80                  85 aag atg att ttg aga acc tct gag gaa acc att tct aca gtt caa gaa        402
Lys Met Ile Leu Arg Thr Ser Glu Glu Thr Ile Ser Thr Val Gln Glu
 90                  95                 100                 105 aag caa caa aat att tct ccc cta gtg aga gaa aga ggt cct cag aga        450
Lys Gln Gln Asn Ile Ser Pro Leu Val Arg Glu Arg Gly Pro Gln Arg
                110                 115                 120 gta gca gct cac ata act ggg acc aga gga aga agc aac aca ttg tct        498
Val Ala Ala His Ile Thr Gly Thr Arg Gly Arg Ser Asn Thr Leu Ser
            125                 130                 135 tct cca aac tcc aag aat gaa aag gct ctg ggc cgc aaa ata aac tcc        546
Ser Pro Asn Ser Lys Asn Glu Lys Ala Leu Gly Arg Lys Ile Asn Ser
        140                 145                 150 tgg gaa tca tca agg agt ggg cat tca ttc ctg agc aac ttg cac ttg        594
Trp Glu Ser Ser Arg Ser Gly His Ser Phe Leu Ser Asn Leu His Leu
    155                 160                 165 agg aat ggt gaa ctg gtc atc cat gaa aaa ggg ttt tac tac atc tat        642
Arg Asn Gly Glu Leu Val Ile His Glu Lys Gly Phe Tyr Tyr Ile Tyr
```

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| 170 |     |     |     |     | 175 |     |     |     |     | 180 |     |     |     |     | 185 |     |

```
tcc caa aca tac ttt cga ttt cag gag gaa ata aaa gaa aac aca aag          690
Ser Gln Thr Tyr Phe Arg Phe Gln Glu Glu Ile Lys Glu Asn Thr Lys
                    190                 195                 200 aac gac aaa caa atg gtc caa tat att tac aaa tac aca agt tat cct          738
Asn Asp Lys Gln Met Val Gln Tyr Ile Tyr Lys Tyr Thr Ser Tyr Pro
            205                 210                 215 gac cct ata ttg ttg atg aaa agt gct aga aat agt tgt tgg tct aaa          786
Asp Pro Ile Leu Leu Met Lys Ser Ala Arg Asn Ser Cys Trp Ser Lys
        220                 225                 230 gat gca gaa tat gga ctc tat tcc atc tat caa ggg gga ata ttt gag          834
Asp Ala Glu Tyr Gly Leu Tyr Ser Ile Tyr Gln Gly Gly Ile Phe Glu
    235                 240                 245 ctt aag gaa aat gac aga att ttt gtt tct gta aca aat gag cac ttg          882
Leu Lys Glu Asn Asp Arg Ile Phe Val Ser Val Thr Asn Glu His Leu
250                 255                 260                 265 ata gac atg gac cat gaa gcc agt ttt ttc ggg gcc ttt tta gtt ggc          930
Ile Asp Met Asp His Glu Ala Ser Phe Phe Gly Ala Phe Leu Val Gly
                270                 275                 280 taa ctgacctgga aagaaaaagc aataacctca aagtgactat tcagttttca              983
ggatgataca ctatgaagat gtttcaaaaa atctgaccaa acaaacaaaa cagaaaacag       1043
aaaacaaaaa aacctctatg caatctgagt agagcagcca caaccaaaaa attctacaac      1103
acacactgtt ctgaaagtga ctcacttatc ccaagaaaat gaaattgctg aaagatcttt       1163
caggactcta cctcatatca gtttgctagc agaaatctag aagactgtca gcttccaaac      1223
attaatgcaa tggttaacat cttctgtctt tataatctac tccttgtaaa gactgtagaa       1283
gaaagcgcaa caatccatct ctcaagtagt gtatcacagt agtagcctcc aggtttcctt      1343
aagggacaac atccttaagt caaagagag aagaggcacc actaaaagat cgcagtttgc       1403
ctggtgcagt ggctcacacc tgtaatccca catttggg aacccaaggt gggtagatca        1463
cgagatcaag agatcaagac catagtgacc aacatagtga aaccccatct ctactgaaag       1523
tgcaaaaatt agctgggtgt gttggcacat gcctgtagtc ccagctactt gagaggctga      1583
ggcaggagaa tcgtttgaac ccgggaggca gaggttgcag tgtggtgaga tcatgccact       1643
acactccagc ctggcgacag agcgagactt ggtttcaaaa aaaaaaaaaa aaaaaaactt      1703
cagtaagtac gtgttatttt tttcaataaa attctattac agtatgtcaa aaaaaaaaaa      1763
aaaaaa                                                                  1769

<210> SEQ ID NO 2
<211> LENGTH: 1407
<212> TYPE: DNA
<213> ORGANISM: H. sapiens
<220> FEATURE:
<221> NAME/KEY: CDS
<222> LOCATION: (1)...(1407)
<223> OTHER INFORMATION: Human TRAIL Receptor Coding Sequence

<400> SEQUENCE: 2 atg gcg cca cca cca gct aga gta cat cta ggt gcg ttc ctg gca gtg           48
Met Ala Pro Pro Pro Ala Arg Val His Leu Gly Ala Phe Leu Ala Val
1               5                   10                  15 act ccg aat ccc ggg agc gca gcg agt ggg aca gag gca gcc gcg gcc           96
Thr Pro Asn Pro Gly Ser Ala Ala Ser Gly Thr Glu Ala Ala Ala Ala
                20                  25                  30 aca ccc agc aaa gtg tgg ggc tct tcc gcg ggg agg att gaa cca cga          144
Thr Pro Ser Lys Val Trp Gly Ser Ser Ala Gly Arg Ile Glu Pro Arg
            35                  40                  45
```

-continued

| | | |
|---|---|---|
| ggc ggg ggc cga gga gcg ctc cct acc tcc atg gga cag cac gga ccc<br>Gly Gly Gly Arg Gly Ala Leu Pro Thr Ser Met Gly Gln His Gly Pro<br>50                              55                       60 | 192 |
| agt gcc cgg gcc cgg gca ggg cgc gcc cca gga ccc agg ccg gcg cgg<br>Ser Ala Arg Ala Arg Ala Gly Arg Ala Pro Gly Pro Arg Pro Ala Arg<br>65                         70                       75                     80 | 240 |
| gaa gcc agc cct cgg ctc cgg gtc cac aag acc ttc aag ttt gtc gtc<br>Glu Ala Ser Pro Arg Leu Arg Val His Lys Thr Phe Lys Phe Val Val<br>                     85                       90                       95 | 288 |
| gtc ggg gtc ctg ctg cag gtc gta cct agc tca gct gca acc atc aaa<br>Val Gly Val Leu Leu Gln Val Val Pro Ser Ser Ala Ala Thr Ile Lys<br>                     100                     105                    110 | 336 |
| ctt cat gat caa tca att ggc aca cag caa tgg gaa cat agc cct ttg<br>Leu His Asp Gln Ser Ile Gly Thr Gln Gln Trp Glu His Ser Pro Leu<br>            115                     120                     125 | 384 |
| gga gag ttg tgt cca cca gga tct cat aga tca gaa cgt cct gga gcc<br>Gly Glu Leu Cys Pro Pro Gly Ser His Arg Ser Glu Arg Pro Gly Ala<br>        130                     135                     140 | 432 |
| tgt aac cgg tgc aca gag ggt gtg ggt tac acc aat gct tcc aac aat<br>Cys Asn Arg Cys Thr Glu Gly Val Gly Tyr Thr Asn Ala Ser Asn Asn<br>145                       150                     155                    160 | 480 |
| ttg ttt gct tgc ctc cca tgt aca gct tgt aaa tca gat gaa gaa gag<br>Leu Phe Ala Cys Leu Pro Cys Thr Ala Cys Lys Ser Asp Glu Glu Glu<br>                    165                     170                    175 | 528 |
| aga agt ccc tgc acc acg acc agg aac aca gca tgt cag tgc aaa cca<br>Arg Ser Pro Cys Thr Thr Thr Arg Asn Thr Ala Cys Gln Cys Lys Pro<br>            180                     185                     190 | 576 |
| gga act ttc cgg aat gac aat tct gct gag atg tgc cgg aag tgc agc<br>Gly Thr Phe Arg Asn Asp Asn Ser Ala Glu Met Cys Arg Lys Cys Ser<br>        195                     200                     205 | 624 |
| aca ggg tgc ccc aga ggg atg gtc aag gtc aag gat tgt acg ccc tgg<br>Thr Gly Cys Pro Arg Gly Met Val Lys Val Lys Asp Cys Thr Pro Trp<br>            210                     215                     220 | 672 |
| agt gac atc gag tgt gtc cac aaa gaa tca ggc aat gga cat aat ata<br>Ser Asp Ile Glu Cys Val His Lys Glu Ser Gly Asn Gly His Asn Ile<br>225                       230                     235                    240 | 720 |
| tgg gtg att ttg gtt gtg act ttg gtt gtt ccg ttg ctg ttg gtg gct<br>Trp Val Ile Leu Val Val Thr Leu Val Val Pro Leu Leu Leu Val Ala<br>                    245                     250                    255 | 768 |
| gtg ctg att gtc tgt tgt tgc atc ggc tca ggt tgt gga ggg gac ccc<br>Val Leu Ile Val Cys Cys Cys Ile Gly Ser Gly Cys Gly Gly Asp Pro<br>            260                     265                     270 | 816 |
| aag tgc atg gac agg gtg tgt ttc tgg cgc ttg ggt ctc cta cga ggg<br>Lys Cys Met Asp Arg Val Cys Phe Trp Arg Leu Gly Leu Leu Arg Gly<br>        275                     280                     285 | 864 |
| cct ggg gct gag gac aat gct cac aac gag att ctg agc aac gca gac<br>Pro Gly Ala Glu Asp Asn Ala His Asn Glu Ile Leu Ser Asn Ala Asp<br>        290                     295                     300 | 912 |
| tcg ctg tcc act ttc gtc tct gag cag caa atg gaa agc cag gag ccg<br>Ser Leu Ser Thr Phe Val Ser Glu Gln Gln Met Glu Ser Gln Glu Pro<br>305                       310                     315                    320 | 960 |
| gca gat ttg aca ggt gtc act gta cag tcc cca ggg gag gca cag tgt<br>Ala Asp Leu Thr Gly Val Thr Val Gln Ser Pro Gly Glu Ala Gln Cys<br>                    325                     330                    335 | 1008 |
| ctg ctg gga ccg gca gaa gct gaa ggg tct cag agg agg agg ctg ctg<br>Leu Leu Gly Pro Ala Glu Ala Glu Gly Ser Gln Arg Arg Arg Leu Leu<br>            340                     345                     350 | 1056 |
| gtt cca gca aat ggt gct gac ccc act gag act ctg atg ctg ttc ttt<br>Val Pro Ala Asn Gly Ala Asp Pro Thr Glu Thr Leu Met Leu Phe Phe | 1104 |

-continued

```
                  355                 360                 365
gac aag ttt gca aac atc gtg ccc ttt gac tcc tgg gac cag ctc atg      1152
Asp Lys Phe Ala Asn Ile Val Pro Phe Asp Ser Trp Asp Gln Leu Met
    370                 375                 380 agg cag ctg gac ctc acg aaa aat gag atc gat gtg gtc aga gct ggt      1200
Arg Gln Leu Asp Leu Thr Lys Asn Glu Ile Asp Val Val Arg Ala Gly
385                 390                 395                 400 aca gca ggc cca ggg gat gcc ttg tat gca atg ctg atg aaa tgg gtc      1248
Thr Ala Gly Pro Gly Asp Ala Leu Tyr Ala Met Leu Met Lys Trp Val
                405                 410                 415 aac aaa act gga cgg aac gcc tcg atc cac acc ctg ctg gat gcc ttg      1296
Asn Lys Thr Gly Arg Asn Ala Ser Ile His Thr Leu Leu Asp Ala Leu
            420                 425                 430 gag agg atg gaa gag aga cat gca aaa gag aag att cag gac ctc ttg      1344
Glu Arg Met Glu Glu Arg His Ala Lys Glu Lys Ile Gln Asp Leu Leu
        435                 440                 445 gtg gac tct gga aag ttc atc tac tta gaa gat ggc aca ggc tct gcc      1392
Val Asp Ser Gly Lys Phe Ile Tyr Leu Glu Asp Gly Thr Gly Ser Ala
    450                 455                 460 gtg tcc ttg gag tga                                                  1407
Val Ser Leu Glu *
465

<210> SEQ ID NO 3
<211> LENGTH: 2161
<212> TYPE: DNA
<213> ORGANISM: H. sapiens
<220> FEATURE:
<221> NAME/KEY: CDS
<222> LOCATION: (256)...(1623)

<400> SEQUENCE: 3
cggcccagtg atcttgaacc ccaaaggcca gaactggagc ctcagtccag agaattctga      60
gaaaattaaa gcagagagga ggggagagat cactgggacc aggccgtgat ctctatgccc     120
gagtctcaac cctcaactgt cacccccaagg cacttgggac gtcctggaca gaccgagtcc    180
cgggaagccc cagcactgcc gctgccacac tgccctgagc ccaaatgggg gagtgagagg    240
ccatagctgt ctggc atg ggc ctc tcc acc gtg cct gac ctg ctg ctg ccg      291
              Met Gly Leu Ser Thr Val Pro Asp Leu Leu Leu Pro
                1               5                   10 ctg gtg ctc ctg gag ctg ttg gtg gga ata tac ccc tca ggg gtt att      339
Leu Val Leu Leu Glu Leu Leu Val Gly Ile Tyr Pro Ser Gly Val Ile
        15                  20                  25 gga ctg gtc cct cac cta ggg gac agg gag aag aga gat agt gtg tgt      387
Gly Leu Val Pro His Leu Gly Asp Arg Glu Lys Arg Asp Ser Val Cys
    30                  35                  40 ccc caa gga aaa tat atc cac cct caa aat aat tcg att tgc tgt acc      435
Pro Gln Gly Lys Tyr Ile His Pro Gln Asn Asn Ser Ile Cys Cys Thr
45                  50                  55                  60 aag tgc cac aaa gga acc tac ttg tac aat gac tgt cca ggc ccg ggg      483
Lys Cys His Lys Gly Thr Tyr Leu Tyr Asn Asp Cys Pro Gly Pro Gly
                65                  70                  75 cag gat acg gac tgc agg gag tgt gag agc ggc tcc ttc acc gct tca      531
Gln Asp Thr Asp Cys Arg Glu Cys Glu Ser Gly Ser Phe Thr Ala Ser
            80                  85                  90 gaa aac cac ctc aga cac tgc ctc agc tgc tcc aaa tgc cga aag gaa      579
Glu Asn His Leu Arg His Cys Leu Ser Cys Ser Lys Cys Arg Lys Glu
        95                  100                 105 atg ggt cag gtg gag atc tct tct tgc aca gtg gac cgg gac acc gtg      627
Met Gly Gln Val Glu Ile Ser Ser Cys Thr Val Asp Arg Asp Thr Val
```

-continued

```
         110                 115                 120
tgt ggc tgc agg aag aac cag tac cgg cat tat tgg agt gaa aac ctt      675
Cys Gly Cys Arg Lys Asn Gln Tyr Arg His Tyr Trp Ser Glu Asn Leu
125                 130                 135                 140 ttc cag tgc ttc aat tgc agc ctc tgc ctc aat ggg acc gtg cac ctc      723
Phe Gln Cys Phe Asn Cys Ser Leu Cys Leu Asn Gly Thr Val His Leu
                145                 150                 155 tcc tgc cag gag aaa cag aac acc gtg tgc acc tgc cat gca ggt ttc      771
Ser Cys Gln Glu Lys Gln Asn Thr Val Cys Thr Cys His Ala Gly Phe
            160                 165                 170 ttt cta aga gaa aac gag tgt gtc tcc tgt agt aac tgt aag aaa agc      819
Phe Leu Arg Glu Asn Glu Cys Val Ser Cys Ser Asn Cys Lys Lys Ser
        175                 180                 185 ctg gag tgc acg aag ttg tgc cta ccc cag att gag aat gtt aag ggc      867
Leu Glu Cys Thr Lys Leu Cys Leu Pro Gln Ile Glu Asn Val Lys Gly
    190                 195                 200 act gag gac tca ggc acc aca gtg ctg ttg ccc ctg gtc att ttc ttt      915
Thr Glu Asp Ser Gly Thr Thr Val Leu Leu Pro Leu Val Ile Phe Phe
205                 210                 215                 220 ggt ctt tgc ctt tta tcc ctc ctc ttc att ggt tta atg tat cgc tac      963
Gly Leu Cys Leu Leu Ser Leu Leu Phe Ile Gly Leu Met Tyr Arg Tyr
                225                 230                 235 caa cgg tgg aag tcc aag ctc tac tcc att gtt tgt ggg aaa tcg aca     1011
Gln Arg Trp Lys Ser Lys Leu Tyr Ser Ile Val Cys Gly Lys Ser Thr
            240                 245                 250 cct gaa aaa gag ggg gag ctt gaa gga act act act aag ccc ctg gcc     1059
Pro Glu Lys Glu Gly Glu Leu Glu Gly Thr Thr Thr Lys Pro Leu Ala
        255                 260                 265 cca aac cca agc ttc agt ccc act cca ggc ttc acc ccc acc ctg ggc     1107
Pro Asn Pro Ser Phe Ser Pro Thr Pro Gly Phe Thr Pro Thr Leu Gly
    270                 275                 280 ttc agt ccc gtg ccc agt tcc acc ttc acc tcc agc tcc acc tat acc     1155
Phe Ser Pro Val Pro Ser Ser Thr Phe Thr Ser Ser Ser Thr Tyr Thr
285                 290                 295                 300 ccc ggt gac tgt ccc aac ttt gcg gct ccc cgc aga gag gtg gca cca     1203
Pro Gly Asp Cys Pro Asn Phe Ala Ala Pro Arg Arg Glu Val Ala Pro
                305                 310                 315 ccc tat cag ggg gct gac ccc atc ctt gcg aca gcc ctc gcc tcc gac     1251
Pro Tyr Gln Gly Ala Asp Pro Ile Leu Ala Thr Ala Leu Ala Ser Asp
            320                 325                 330 ccc atc ccc aac ccc ctt cag aag tgg gag gac agc gcc cac aag cca     1299
Pro Ile Pro Asn Pro Leu Gln Lys Trp Glu Asp Ser Ala His Lys Pro
        335                 340                 345 cag agc cta gac act gat gac ccc gcg acg ctg tac gcc gtg gtg gag     1347
Gln Ser Leu Asp Thr Asp Asp Pro Ala Thr Leu Tyr Ala Val Val Glu
    350                 355                 360 aac gtg ccc ccg ttg cgc tgg aag gaa ttc gtg cgg cgc cta ggg ctg     1395
Asn Val Pro Pro Leu Arg Trp Lys Glu Phe Val Arg Arg Leu Gly Leu
365                 370                 375                 380 agc gac cac gag atc gat cgg ctg gag ctg cag aac ggg cgc tgc ctg     1443
Ser Asp His Glu Ile Asp Arg Leu Glu Leu Gln Asn Gly Arg Cys Leu
                385                 390                 395 cgc gag gcg caa tac agc atg ctg gcg acc tgg agg cgg cgc acg ccg     1491
Arg Glu Ala Gln Tyr Ser Met Leu Ala Thr Trp Arg Arg Arg Thr Pro
            400                 405                 410 cgg cgc gag gcc acg ctg gag ctg ctg gga cgc gtg ctc cgc gac atg     1539
Arg Arg Glu Ala Thr Leu Glu Leu Leu Gly Arg Val Leu Arg Asp Met
        415                 420                 425 gac ctg ctg ggc tgc ctg gag gac atc gag gag gcg ctt tgc ggc ccc     1587
```

```
                Asp Leu Leu Gly Cys Leu Glu Asp Ile Glu Glu Ala Leu Cys Gly Pro
                    430                 435                 440 gcc gcc ctc ccg ccc gcg ccc agt ctt ctc aga tga ggctgcgccc                    1633
Ala Ala Leu Pro Pro Ala Pro Ser Leu Leu Arg  *
445                 450                 455 ctgcgggcag ctctaaggac cgtcctgcga gatcgccttc caaccccact tttttctgga             1693
aaggaggggt cctgcagggg caagcaggag ctagcagccg cctacttggt gctaaccect             1753 cgatgtacat agcttttctc agctgcctgc gcgccgccga cagtcagcgc tgtgcgcgcg             1813
gagagaggtg cgccgtgggc tcaagagcct gagtgggtgg tttgcgagga tgagggacgc             1873
tatgcctcat gcccgttttg ggtgtcctca ccagcaaggc tgctcggggg cccctggttc             1933
gtccctgagc cttttcaca gtgcataagc agttttttt gttttgttt tgttttgttt               1993 tgttttaaa tcaatcatgt tacactaata gaaacttggc actcctgtgc cctctgcctg             2053
gacaagcaca tagcaagctg aactgtccta aggcaggggc gagcacgaa caatgggcc               2113 ttcagctgga gctgtggact tttgtacata cactaaaatt ctgaagtt                         2161

<210> SEQ ID NO 4
<211> LENGTH: 1643
<212> TYPE: DNA
<213> ORGANISM: H. sapiens
<220> FEATURE:
<221> NAME/KEY: CDS
<222> LOCATION: (153)...(854)

<400> SEQUENCE: 4
gcagaggacc agctaagagg gagagaagca actacagacc cccctgaaa acaaccctca              60 gacgccacat cccctgacaa gctgccaggc aggttctctt cctctcacat actgacccac            120
ggctccaccc tctctcccct ggaaaggaca cc atg agc act gaa agc atg atc              173
                                    Met Ser Thr Glu Ser Met Ile
                                      1               5 cgg gac gtg gag ctg gcc gag gag gcg ctc ccc aag aag aca ggg ggg              221
Arg Asp Val Glu Leu Ala Glu Glu Ala Leu Pro Lys Lys Thr Gly Gly
        10                  15                  20 ccc cag ggc tcc agg cgg tgc ttg ttc ctc agc ctc ttc tcc ttc ctg              269
Pro Gln Gly Ser Arg Arg Cys Leu Phe Leu Ser Leu Phe Ser Phe Leu
    25                  30                  35 atc gtg gca ggc gcc acc acg ctc ttc tgc ctg ctg cac ttt gga gtg              317
Ile Val Ala Gly Ala Thr Thr Leu Phe Cys Leu Leu His Phe Gly Val
40                  45                  50                  55 atc ggc ccc cag agg gaa gag ttc ccc agg gac ctc tct cta atc agc              365
Ile Gly Pro Gln Arg Glu Glu Phe Pro Arg Asp Leu Ser Leu Ile Ser
                60                  65                  70 cct ctg gcc cag gca gtc aga tca tct tct cga acc ccg agt gac aag              413
Pro Leu Ala Gln Ala Val Arg Ser Ser Ser Arg Thr Pro Ser Asp Lys
            75                  80                  85 cct gta gcc cat gtt gta gca aac cct caa gct gag ggg cag ctc cag              461
Pro Val Ala His Val Val Ala Asn Pro Gln Ala Glu Gly Gln Leu Gln
        90                  95                 100 tgg ctg aac cgc cgg gcc aat gcc ctc ctg gcc aat ggc gtg gag ctg              509
Trp Leu Asn Arg Arg Ala Asn Ala Leu Leu Ala Asn Gly Val Glu Leu
    105                 110                 115 aga gat aac cag ctg gtg gtg cca tca gag ggc ctg tac ctc atc tac              557
Arg Asp Asn Gln Leu Val Val Pro Ser Glu Gly Leu Tyr Leu Ile Tyr
120                 125                 130                 135 tcc cag gtc ctc ttc aag ggc caa ggc tgc ccc tcc acc cat gtg ctc              605
Ser Gln Val Leu Phe Lys Gly Gln Gly Cys Pro Ser Thr His Val Leu
                140                 145                 150
```

```
ctc acc cac acc atc agc cgc atc gcc gtc tcc tac cag acc aag gtc        653
Leu Thr His Thr Ile Ser Arg Ile Ala Val Ser Tyr Gln Thr Lys Val
            155                 160                 165 aac ctc ctc tct gcc atc aag agc ccc tgc cag agg gag acc cca gag        701
Asn Leu Leu Ser Ala Ile Lys Ser Pro Cys Gln Arg Glu Thr Pro Glu
            170                 175                 180 ggg gct gag gcc aag ccc tgg tat gag ccc atc tat ctg gga ggg gtc        749
Gly Ala Glu Ala Lys Pro Trp Tyr Glu Pro Ile Tyr Leu Gly Gly Val
185                 190                 195 ttc cag ctg gag aag ggt gac cga ctc agc gct gag atc aat cgg ccc        797
Phe Gln Leu Glu Lys Gly Asp Arg Leu Ser Ala Glu Ile Asn Arg Pro
200                 205                 210                 215 gac tat ctc gac ttt gcc gag tct ggg cag gtc tac ttt ggg atc att        845
Asp Tyr Leu Asp Phe Ala Glu Ser Gly Gln Val Tyr Phe Gly Ile Ile
                220                 225                 230 gcc ctg tga ggaggacgaa catccaacct tcccaaacgc ctcccctgcc                894
Ala Leu * ccaatcccett tattaccccc tccttcagac accctcaacc tcttctggct caaaaagaga    954
attgggggct tagggtcgga acccaagctt agaactttaa gcaacaagac caccacttcg    1014
aaacctggga ttcaggaatg tgtggcctgc acagtgaatt gctggcaacc actaagaatt    1074
caaactgggg cctccagaac tcactggggc ctacagcttt gatccctgac atctggaatc    1134
tggagaccag ggagcctttg gttctggcca gaatgctgca ggacttgaga agacctcacc    1194
tagaaattga cacaagtgga ccttaggcct tcctctctcc agatgtttcc agacttcctt    1254
gagacacgga gcccagccct ccccatggag ccagctccct ctatttatgt ttgcacttgt    1314
gattatttat tatttattta ttatttattt atttacagat gaatgtattt atttgggaga    1374
ccggggtatc ctgggggacc caatgtagga gctgccttgg ctcagacatg ttttccgtga    1434
aaacggagct gaacaatagg ctgttcccat gtagccccct ggcctctgtg ccttcttttg    1494 attatgttttt ttaaaatatt tatctgatta agttgtctaa acaatgctga tttggtgacc   1554
aactgtcact cattgctgag cctctgctcc ccaggggagt tgtgtctgta atcgccctac    1614
tattcagtgg cgagaaataa agtttgctt                                       1643
```